United States Patent
Spehr

Patent Number: 6,134,478
Date of Patent: Oct. 17, 2000

[54] METHOD FOR MAKING CARDIAC LEADS WITH ZONE INSULATED ELECTRODES

[75] Inventor: Paul R. Spehr, Lake Jackson, Tex.

[73] Assignee: Intermedics Inc., Angleton, Tex.

[21] Appl. No.: 09/366,400

[22] Filed: Aug. 3, 1999

Related U.S. Application Data

[63] Continuation-in-part of application No. 09/092,106, Jun. 5, 1998.

[51] Int. Cl.[7] ..................................................... A61N 1/05
[52] U.S. Cl. ............................ 607/115; 600/373; 607/116
[58] Field of Search ................................... 607/116, 119, 607/122, 115; 600/373

[56] References Cited

U.S. PATENT DOCUMENTS

| | | | |
|---|---|---|---|
| 3,911,928 | 10/1975 | Lagergren | 128/418 |
| 4,026,303 | 5/1977 | Babotai | 128/418 |
| 4,044,774 | 8/1977 | Corbin et al. | 128/404 |
| 4,440,178 | 4/1984 | Bussard et al. | 128/784 |
| 4,502,492 | 3/1985 | Bornzin | 128/785 |
| 4,611,604 | 9/1986 | Botvidsson et al. | 128/784 |
| 4,630,611 | 12/1986 | King | 128/642 |
| 4,649,937 | 3/1987 | DeHaan et al. | 128/784 |
| 4,760,852 | 8/1988 | Lekholm | 128/785 |
| 4,765,341 | 8/1988 | Mower et al. | 128/785 |
| 5,222,506 | 6/1993 | Patrick et al. | 128/784 |
| 5,231,996 | 8/1993 | Bardy et al. | 128/785 |
| 5,324,322 | 6/1994 | Grill, Jr. et al. | 607/118 |
| 5,405,373 | 4/1995 | Petersson et al. | 607/121 |
| 5,405,375 | 4/1995 | Ayers et al. | 607/122 |
| 5,456,254 | 10/1995 | Pietroski et al. | 607/116 |
| 5,514,173 | 5/1996 | Rebell et al. | 607/127 |
| 5,515,848 | 5/1996 | Corbett, III et al. | 607/116 |
| 5,522,877 | 6/1996 | Garfield et al. | 607/138 |
| 5,579,764 | 12/1996 | Goldreyer | 607/122 |
| 5,658,321 | 8/1997 | Fayram | 607/36 |
| 5,779,699 | 7/1998 | Lipson | 606/41 |
| 5,782,900 | 7/1998 | de la Rama et al. | 607/122 |
| 5,785,706 | 7/1998 | Bednarek | 607/119 |
| 5,807,399 | 9/1998 | Laske et al. | 607/126 |
| 5,836,874 | 11/1998 | Swanson et al. | 600/374 |
| 5,860,974 | 1/1999 | Abele | 606/41 |
| 5,871,529 | 2/1999 | Bartig et al. | 607/122 |
| 5,871,531 | 2/1999 | Struble | 607/126 |
| 5,871,532 | 2/1999 | Schroeppel | 607/128 |
| 5,873,894 | 2/1999 | Vandegriff et al. | 607/9 |
| 5,876,408 | 3/1999 | Alt et al. | 606/129 |
| 5,876,424 | 3/1999 | O'Phelan et al. | 607/36 |
| 5,876,431 | 3/1999 | Spehr et al. | 607/126 |
| 5,885,221 | 3/1999 | Hsu et al. | 600/515 |
| 5,908,447 | 6/1999 | Schroeppel et al. | 607/126 |
| 5,913,887 | 6/1999 | Michel | 607/123 |
| 5,916,238 | 6/1999 | Hauser et al. | 607/5 |
| 5,925,069 | 7/1999 | Graves et al. | 607/36 |
| 5,925,073 | 7/1999 | Chastain et al. | 607/122 |
| 5,931,858 | 8/1999 | Kadhiresan et al. | 607/20 |
| 5,931,864 | 8/1999 | Chastain et al. | 607/128 |

(List continued on next page.)

FOREIGN PATENT DOCUMENTS

| | | | |
|---|---|---|---|
| 0054781 | 6/1982 | European Pat. Off. | A61N 1/04 |
| 0191238 | 8/1988 | European Pat. Off. | A61N 1/05 |
| 0296001 | 12/1988 | European Pat. Off. | A61N 1/05 |
| 2225179 | 11/1974 | France | A61N 1/04 |
| 93/00130 | 1/1993 | WIPO | A61N 1/05 |

*Primary Examiner*—Carl H. Layno
*Attorney, Agent, or Firm*—Schwegmen, Lundberg, Woessner & Kluth, P.A.

[57] ABSTRACT

An electrode for a cardiac lead and method of making the same are provided. The electrode includes an electrode member and a coating applied to the electrode member. A method of fabricating a high impedance cardiac lead electrode is provided. The method includes the steps of providing an electrode member and coating a first portion of the electrode member with an electrically insulating material and placing a tubular mask or shield over the electrode. Portions of the insulating material are removed to expose selected areas of the electrode. The second or exposed portion enhances the impedance of the electrode, resulting in power savings and extended life spans for implantable stimulation and sensing devices. Exemplary materials for the coating includes diamond-like carbon and sapphire.

10 Claims, 6 Drawing Sheets

U.S. PATENT DOCUMENTS

| | | | |
|---|---|---|---|
| 5,935,154 | 8/1999 | Westlund | 607/36 |
| 5,935,160 | 8/1999 | Auricchio et al. | 607/122 |
| 5,935,465 | 8/1999 | Cardineau et al. | 219/121 |
| 5,941,903 | 8/1999 | Zhu et al. | 607/13 |
| 5,941,904 | 8/1999 | Johnston et al. | 607/19 |
| 5,944,744 | 8/1999 | Paul et al. | 607/9 |
| 5,951,597 | 9/1999 | Westlund et al. | 607/126 |
| 5,954,753 | 9/1999 | Alt et al. | 607/8 |
| 5,957,966 | 9/1999 | Schroeppel et al. | 607/122 |
| 5,978,707 | 11/1999 | Krig et al. | 607/14 |
| 5,978,710 | 11/1999 | Prutchi et al. | 607/17 |
| 5,983,138 | 11/1999 | Kramer | 607/9 |
| 5,989,077 | 11/1999 | Mast et al. | 439/814 |
| 5,991,657 | 11/1999 | Kim | 607/5 |
| 5,991,662 | 11/1999 | Kim et al. | 607/27 |
| 6,002,969 | 12/1999 | Machek et al. | 607/122 |
| 6,018,684 | 1/2000 | Bartig et al. | 607/122 |

METHOD FOR MAKING CARDIAC LEADS WITH ZONE INSULATED ELECTRODES

This application is a continuation-in-part of U.S. patent application Ser. No. 09/092,106, filed Jun. 5, 1998, which is incorporated herein by reference.

BACKGROUND OF THE INVENTION

1. Field of the Invention

This invention relates generally to cardiac stimulator leads, and more particularly to a cardiac stimulator lead having an electrode selectively coated with an insulating material to define small conductive regions.

2. Description of the Related Art

Conventional cardiac stimulator systems consist of a cardiac stimulator and an elongated flexible cardiac lead that is connected proximally to a header structure on the cardiac stimulator and is implanted distally at one or more sites within the heart requiring cardiac stimulation or sensing. The cardiac stimulator is normally a pacemaker, a cardioverter/defibrillator, a sensing instrument, or some combination of these devices.

At the time of implantation, the distal end of a cardiac lead is inserted through an incision in the chest and manipulated by the physician to the site requiring electrical stimulation with the aid of a flexible stylet that is removed prior to closure. At the site requiring electrical stimulation, the distal end of the lead is anchored to the endocardium by an active mechanism, such as a screw-in electrode tip, or alternatively, by a passive mechanism, such as one or more radially spaced tines. The proximal end of the lead is then connected to the cardiac stimulator and the incision is closed.

Many implantable cardiac stimulators include a microprocessor or control circuit enclosed within a sealed housing or can. The circuit board controls the delivery of electric pulses to the lead and may perform various other functions. Power is supplied by an internal battery.

A conventional cardiac stimulator lead normally consists of an elongated, flexible, tubular, electrically insulating sleeve connected proximally to a connector that is adapted to couple to the header of a cardiac stimulator can and connected distally to a tubular tip electrode. One or more ring-type electrodes may be secured to the sleeve at various positions along the length of the sleeve. The proximal end of the lead sleeve is connected to the connector by application of various biocompatible adhesives to various portions of the connector and the sleeve. The tip electrode ordinarily consists of a tubular structure that has an increased diameter portion that forms an annular shoulder against which the distal end of the lead sleeve abuts. The exterior surface of the tubular structure is normally smooth as is the interior surface of the distal end of the lead sleeve. In multi-polar leads, one or more ring-type electrodes may be fitted over the sleeve.

To ensure that physical contact with the desired myocardial tissue is maintained after implantation, tip electrodes for most conventional leads are anchored to myocardial tissue by a fixation mechanism of one sort or another. In some leads, a corkscrew-like member projects from the tip electrode and penetrates the endocardium. In others, the electrode is fitted with one or more radially projecting tines that engage the trabeculae within the heart. Still others may employ both types of structures.

Most conventional tip electrodes serve at least two functions. First, tip electrodes provide a conducting member to convey electrical stimulation and sensing signals to and from myocardial tissue. Second, most tip electrodes provide structure to accommodate a fixation mechanism. Although conventional ring electrodes may be fitted with tines, most ring electrodes serve primarily as signal conductors.

The design of cardiac stimulation systems involves a balancing of a number of competing design considerations. Some of these include can size, lead tip dimensions and power consumption. Can miniaturization has been an important design goal since the first implantable pacemakers were introduced over thirty years ago. Smaller cans yield better post-operative comfort and cosmetic results for the patient. However, can miniaturization has required downsizing in storage batteries, which has, in turn, placed a premium on power consumption. Power consumption is of great importance because for a given level of power consumption, smaller batteries generally translate into shorter cardiac stimulator life spans and more frequent surgical procedures for the patient.

Some of the limitations associated with diminishing battery size have been offset by advances in cell chemistry. In addition, advances in pulse generation circuitry have dramatically increased the efficiency of power consumption. For example, many cardiac stimulators incorporate circuitry that automatically tailors pulse generation to the physiological demands of the patient.

However, despite advances in battery chemistry and circuitry, power consumption efficiency is still frequently limited by conventional lead electrode design. Most conventional lead electrodes operate as relatively low impedance, and thus, high current drawing devices. The low impedance levels are primarily a function of the relatively large conducting surface areas that these devices present to myocardial tissue. As noted above, the size of conventional lead electrodes is dictated in large part by mechanical considerations, such as the facilitation of fixation mechanisms. Furthermore, a certain degree of bluntness in a tip electrode is desirable to reduce the risk of myocardial perforation and micro-dislodgement, and to facilitate capture of the lead tip by post-implant developing fibrous tissue. Similarly, miniaturization of ring-type electrodes is generally limited by the size of the insulating lead sleeve and by the prevailing mechanical systems used to secure such ring-type electrodes to the lead sleeve.

As a result of these mechanical design considerations, current is often drawn by conventional low impedance electrodes at higher rates than necessary for appropriate stimulation. Some improvement in current drain may be realized by lowering the voltage output of the pulse generator. However, this technique is not possible in patients who require a threshold voltage for successful stimulation that is above the contemplated lowered output voltage. Thus, conventional lead electrode designs may represent an impediment to extended battery life.

In one conventional lead design, the distal end of the lead is provided with a distally projecting, small diameter circular electrode that has the potential to provide enhanced pacing impedance. However, this design may be prone to micro-dislodgment. Since the lead is provided with a single small conducting surface on the distal end of the lead, normal heart motion may cause the small conducting surface to momentarily lose contact with or micro-dislodge from myocardial tissue and disrupt the flow of pacing pulses.

The present invention is directed to overcoming or reducing the effects of one or more of the foregoing disadvantages.

SUMMARY OF THE INVENTION

In accordance with the present invention, a method of fabricating a high impedance cardiac lead electrode is provided. The method includes the steps of providing an electrode member and coating a first portion of the electrode member with an electrically insulating material and placing a tubular mask or shield over the electrode. Portions of the insulating material are removed to expose selected areas of the electrode.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
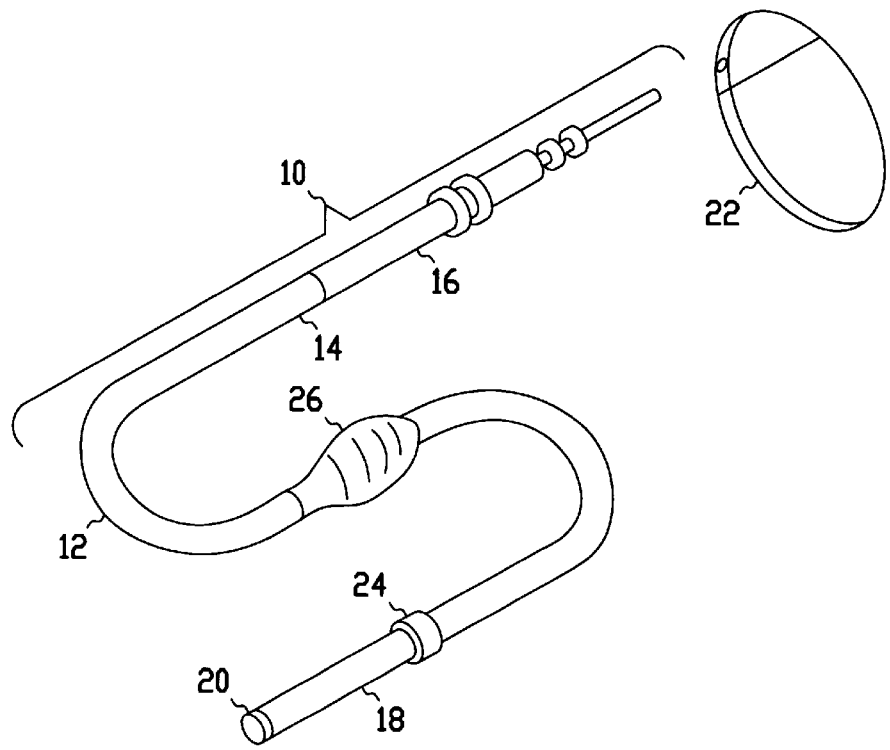
FIG. 1 is a pictorial view of an exemplary embodiment of a cardiac stimulator lead and a cardiac stimulator in accordance with the present invention.

In the drawings described below, reference numerals are generally repeated where identical elements appear in more than one figure. Turning now to the drawings, and in particular to FIG. 1, there is shown an exemplary cardiac stimulator lead 10 that includes a flexible insulating sleeve 12 that has a proximal end 14 coupled to a connector 16, and a distal end 18 coupled to a tip electrode 20. The connector 16 is designed to be inserted into a cardiac stimulator 22, and is shown highly exaggerated in size relative to the cardiac stimulator 22. The cardiac stimulator 22 may be a pacemaker, a cardioverter/defibrillator, or other type of stimulator or a sensing instrument. The illustrated embodiment of the lead 10 is bipolar. Accordingly, the distal end 18 is provided with an electrode 24 located proximal to the tip electrode 20. However, unipolar or other multi-polar arrangements are possible as well. A suture sleeve 26 is slipped over the sleeve 12. During implantation, the suture sleeve 26 is sewn to body tissue at the site of transvenous entry.

The sleeve 12 is a flexible tubular member that provides a robust, electrically insulating coupling between the connector 16 and the electrode 20. The sleeve 12 protects one or more fine gage conductor wires enclosed therein from body fluids and tissues, and is advantageously composed of a biocompatible, electrically insulating material, such as silicone, polyurethane, or like materials.

Figure 2:
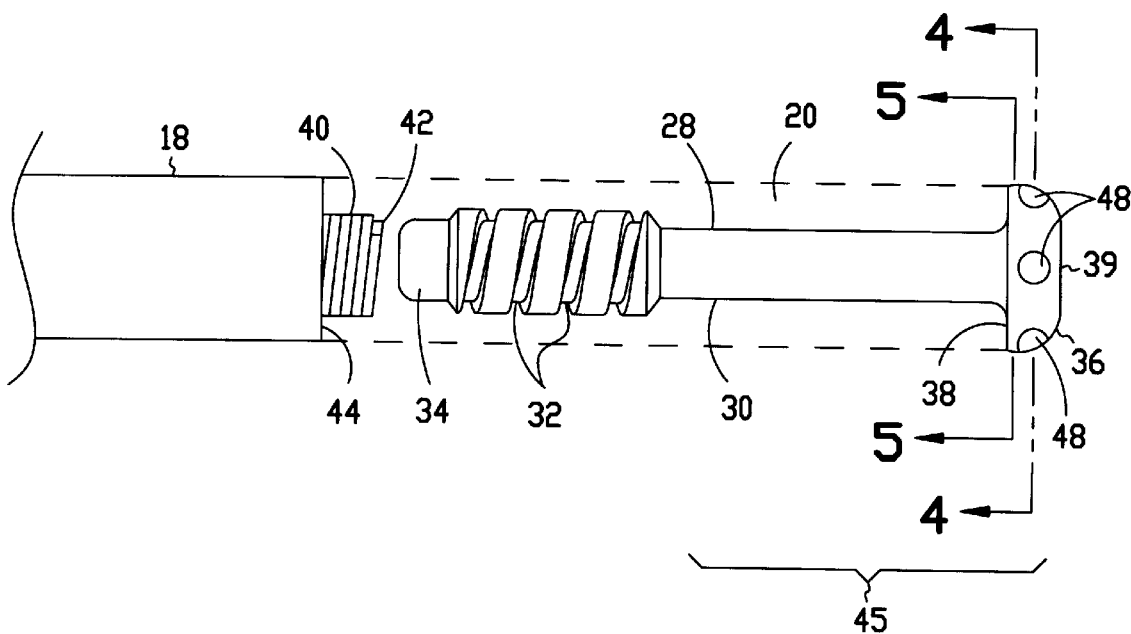
FIG. 2 is an exploded side view of an exemplary cardiac lead electrode, sleeve and conductor in accordance with the present invention.
Figure 3:
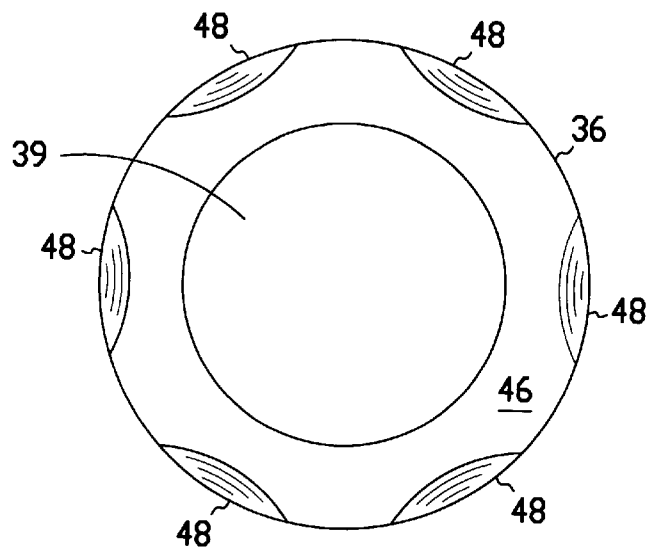
FIG. 3 is an end view of the electrode shown in FIG. 2 in accordance with the present invention.

The detailed structure of the electrode 20 may be understood by referring now also to FIG. 2, which is an exploded side view of the electrode 20 and the end 18 of the sleeve positioned distal from the electrode 24, and to FIG. 3 which is an end view of FIG. 2. The electrode 20 includes an electrode member 28 that has an elongated mandrel-like shank 30 that is provided with a set of external grooves or threads 32 at its proximal end 34 and terminates in an enlarged diameter tip 36. The grooves 32 may be formed integrally with the shank 30 or machined as a separate structure that may be welded or otherwise connected to the shank 30. The transition from the shank 30 to the larger diameter tip 36 defines a proximally facing annular shoulder 38. The tip 36 has a profile that tapers inwardly to a circular blunt or flat end surface 39. Although the profile of the tip 36 is largely a matter of design discretion, an overall blunt profile of the distal end of the tip 36 reduces the potential for myocardial penetration and micro-dislodgment.

The electrode member 28 is advantageously fabricated from a biocompatible conductor or semiconductor material. Suitable materials include, for example, iridium oxide coated titanium, MP35N, stainless steel, platinum-iridium alloy consisting of approximately 90% platinum and 10% iridium, or some other biocompatible conducting metal, or a semiconductor material, such as silicon, or other semiconductor material. A portion of the electrode 20 may be composed of other than a conducting material so long as a conducting pathway is provided between the conductor wire 40 and the tip 36.

A conductor wire 40, shown exploded from the electrode 20, is slipped over the proximal end 34 of the shank 30 and spiraled around the grooves 32 when the lead 10 is assembled. The wire 40 is depicted as a coiled metallic conductor wire that is individually insulated with a thin insulating jacket. An end 42 of the wire 40 is stripped as shown to establish a good electrical contact with the exterior of the shank 30. The end 42 may also be spot welded by laser or other suitable techniques to the exterior of the shank 30. The proximal end of the wire 40 is coupled to the connector 16 shown in FIG. 1. A second conductor wire (not shown) is nested with the conductor wire 40 and is coupled distally to the annular electrode 24 and proximally to the connector 16, and is positioned in a nested arrangement with the wire 40 within the sleeve 12. The skilled artisan will appreciate that other wiring arrangements may be incorporated in lieu of the individually insulated wire 40 and the companion wire (not shown). For example, commonly used coaxial wiring arrangements may be incorporated where the individual wire coils are separated by an inner elongated tubular insulating sleeve.

When the lead 10 is fully assembled, the distal end 18 is slipped over the shank 30 until a distally facing annular shoulder 44 on the distal end 18 abuts the proximally facing annular shoulder 38 of the tip 36. A suitable medical grade, biocompatible adhesive may be applied to the exterior of the shank 30 and/or the interior of the distal end 18 to secure the distal end 18 to the electrode member 28. The adhesive may be a silicone based adhesive, or one of a variety of commercially available two stage biocompatible adhesives.

As noted above, a low impedance electrode in a cardiac lead can result in power consumption that is beyond the rate necessary for medically indicated cardiac stimulation and/or sensing. Although power supply depletion is inevitable in self-contained cells, unnecessary power consumption represents a real limit on battery life. However, in accordance with the present invention, the electrode 20 may be fabricated with a higher impedance than would otherwise be possible in view of the conducting nature and structural requirements of the electrode 20. A lead fitted with the electrode 20 in accordance with the present invention may reduce power consumption and prolong battery life for the cardiac stimulator 22 without sacrificing stimulation and/or sensing functions.

Figure 4:
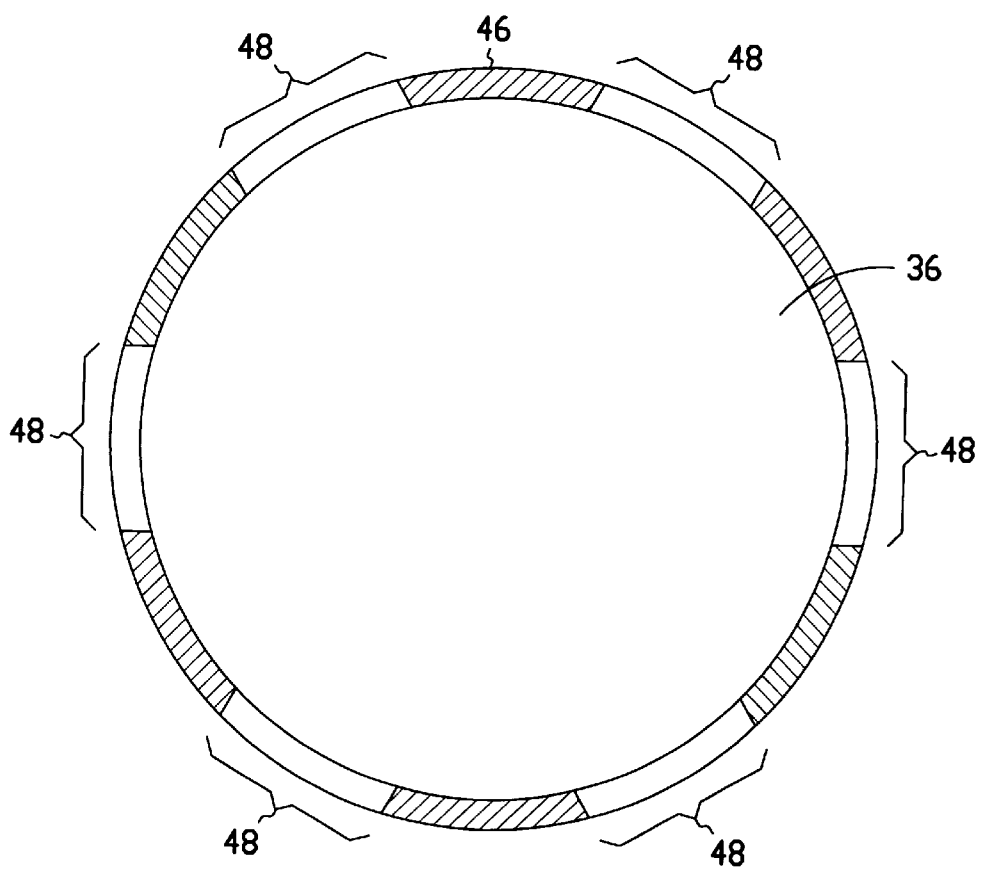
FIG. 4 is a cross-sectional view of FIG. 2 taken at section 44 in accordance with the present invention.
Figure 5:
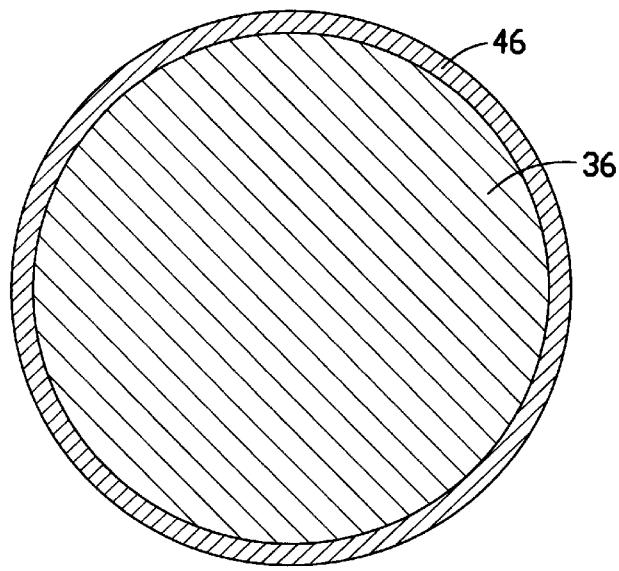
FIG. 5 is a cross-sectional view like FIG. 4 showing the electrode prior to coating with an insulating material in accordance with the present invention.

The impedance enhanced character of the electrode 20 may be understood now by referring to FIGS. 2, 3, 4, and 5. Relative to FIG. 2, FIG. 3 is an end view, and FIGS. 4 and 5 are sectional views taken, respectively, at sections 4—4 and 5—5. A first portion 45 of the exterior of the electrode member 28 from the distal end of the grooves 32 to the end 39 of the tip 36 is covered by a coating 46 composed of an electrically insulating material. A preselected second portion of the exterior of the electrode member 28 consisting of six peripherally spaced, circular spots 48 on the tip 36 is re-exposed, as will be explained below. The coating 46 substantially reduces the otherwise available conducting surface area of the electrode member 28. The exposed circular areas or spots 48 provide small conducting surfaces to contact and transmit electrical current between the electrode 20 and myocardial tissue. The reduced surface area of the electrode member 28 that may be exposed to myocardial tissue dramatically increases the impedance of the electrode 20, thus lowering the power consumption of the lead 10, and increasing the operating life of the power supply for the cardiac stimulator 22 shown in FIG. 1.

In the embodiment illustrated in FIGS. 2, 3, 4, and 5, the first portion 45 of the electrode member 28 includes all of the exterior of the electrode member 28, save the exposed areas 48, the grooves 32, and the proximal end 34. This configuration is illustrative as the desired increase in electrode impedance may be realized when the coating 46 is applied to at least the portion of the electrode member 28 that will be in contact with myocardial tissue. The skilled artisan will appreciate that enhanced impedance may also be achieved by covering a greater or a lesser amount of the exterior of the electrode member 28. For example, the grooves 32 may also be coated if provision is made to establish a conducting connection between the stripped end 42 of the wire 40 and the grooves 32. Conversely, the coating 46 may be applied only to the portion of the electrode member 28 that will contact myocardial tissue, i.e., the tip 36, exclusive of the proximally facing annular shoulder 38.

Figure 6:
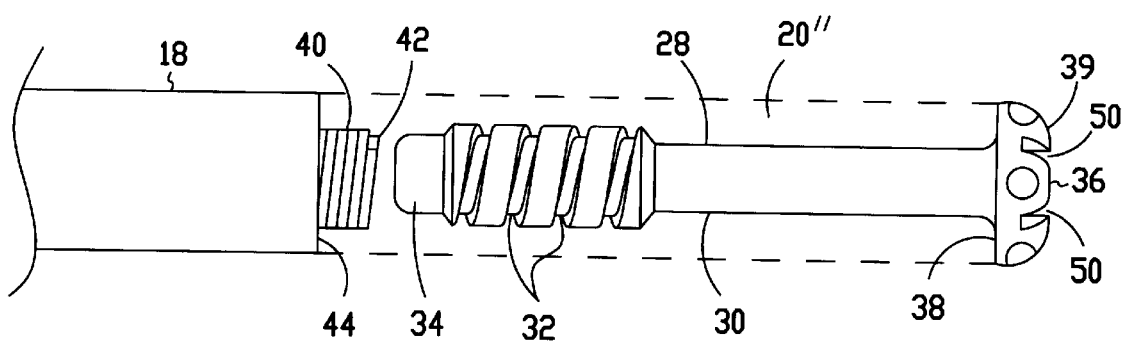
FIG. 6 is an exploded side view like FIG. 2 of an alternate exemplary electrode in accordance with the present invention.
Figure 7:
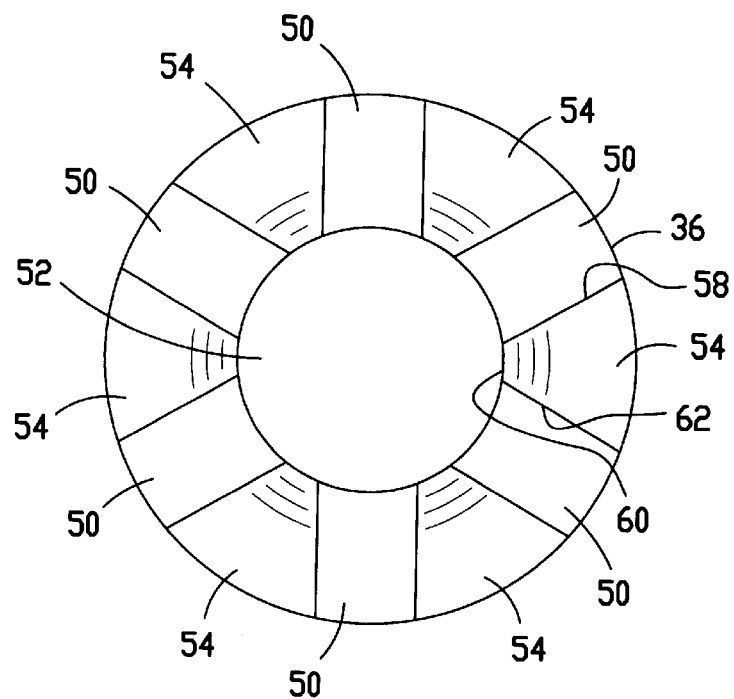
FIG. 7 is an end view of the electrode depicted in FIG. 6 in accordance with the present invention.

The size, and configuration of the portion of the exterior of the electrode member 28 that is exposed following application of the coating 46 is largely a matter of design discretion and will depend on factors such as the electrical requirements of the cardiac stimulator and the medically indicated stimulation voltage, among others. For example, as shown in FIG. 6, which is a side view of an alternate embodiment of the electrode, now designated 20', may be understood by referring now to FIGS. 6 and 7, which are, respectively, an exploded side view and an end view of the electrode 20'. In this embodiment, the tip 36 of the electrode member 28 is provided with six peripherally spaced slots 50 that commonly intersect a circular bore 52. The slots 50 divide the tip 36 into a corresponding number of peripherally spaced projections 54. Each projection 54 has vertical sidewalls 58, 60, and 62.

Polymeric coatings, such as parylene compounds, may be applied using a tool appropriate for the particular material. For example, Parylene C may be applied using a parylene vacuum deposition system which delivers poly-para-xylylene into a vacuum chamber containing the targeted structure, e.g., the electrode member 28.

Figure 8:
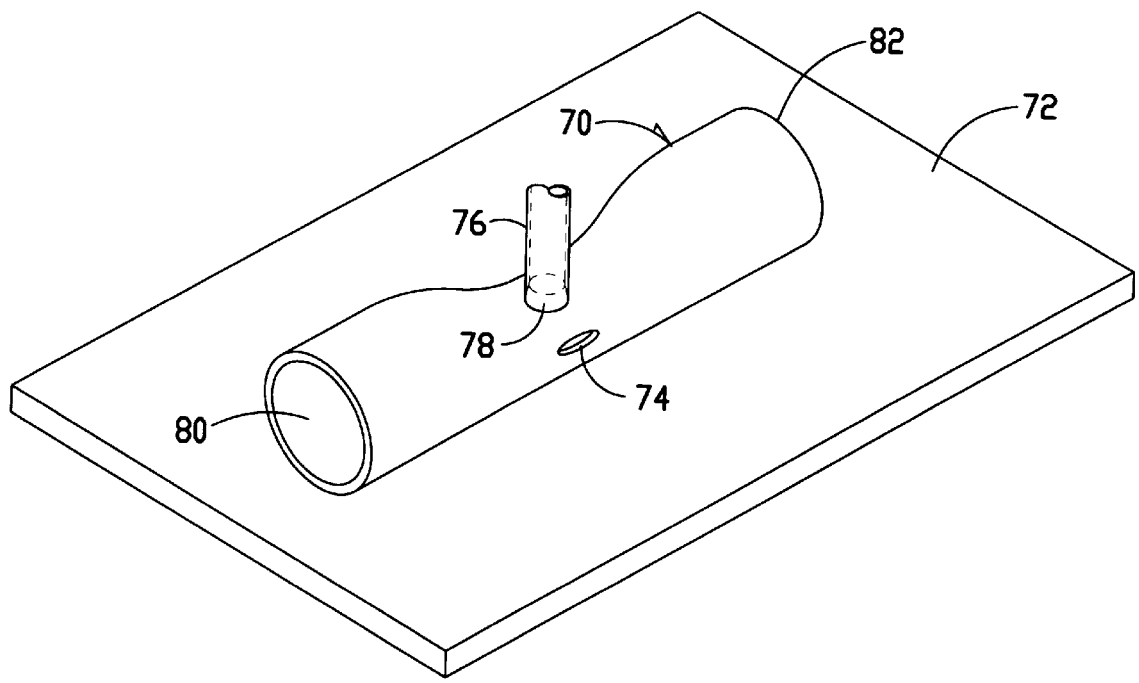
FIG. 8 is a perspective view of a tubular shield being prepared for use in the method of the present invention.
Figure 9:
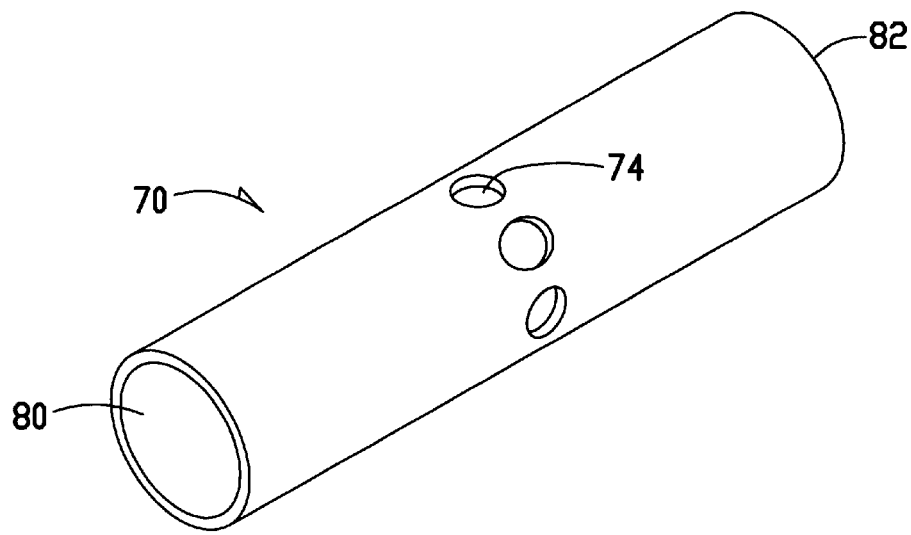
FIG. 9 is a perspective view of the prepared shield of FIG. 8.

After the polymeric coating has been applied to the electrode, selected areas of the coating are removed to expose the conductive surface under the coating. This is accomplished by applying an abrasive process through a mask or shield. Plasma etching is a suitable abrasive process where a parylene compound is used for the coating 46. A tubular sleeve 70, having a proximal end 80 and a distal end 82, includes a pre-selected pattern of openings 74 corresponding to the pre-selected pattern of spots 48. The sleeve should be composed of a material that will withstand the removal process while protecting those portions of the coating 46 that are intended to remain intact. Preferably, the tube is comprised of medical grade silicon rubber. As illustrated in FIG. 8, the sleeve 70 is prepared by placing it on an anvil 72 or support table. A punch 76 is driven through the sleeve to form a circumferential set of holes or openings 74. The punch may be a tube having a beveled cutting edge 78. Other shapes are, of course, feasible. Driving the punch through the sleeve 70 into the anvil 72 produces two diametrically opposed holes. This method produces an even number of openings, for example four or six openings, spaced around the circumference of the sleeve, as shown in FIG. 9.

Figure 10:
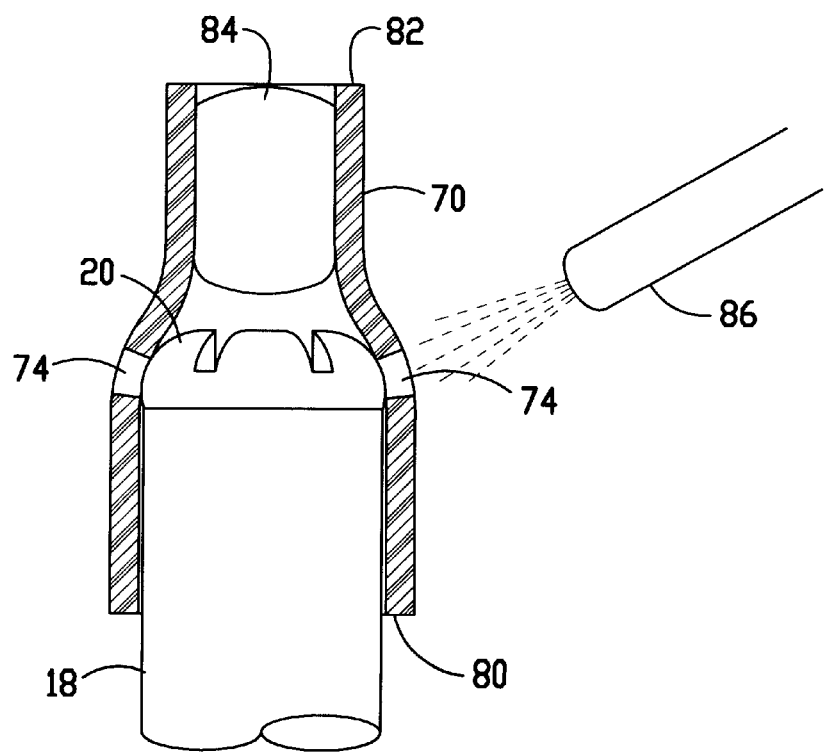
FIG. 10 is a cross sectional view of an electrode tip with shield.

After the holes 74 have been punched in the sleeve, the sleeve is placed over the tip electrode 20 as shown in FIG. 10. Heptane may be used to expand the silicon tube slightly, making it easier to place the sleeve on the electrode tip. The shield is oriented so that the holes 74 are located over those areas where exposure of the conducting portion of the electrode is desired. For example, in the hexagonally notched electrode tip illustrated in FIG. 10 and described in connection with FIG. 6 and FIG. 7 above, the holes could be placed adjacent each segment 54. After the sleeve is placed over the tip, the distal end 82 of the sleeve is filled with medical grade adhesive, forming a complete shield around the tip. The tip is then exposed to plasma from a plasma source 86 to abrade the polymeric coating. After the polymeric coating has been removed in the desired locations, the sleeve is removed from the electrode tip.

Figure 11:
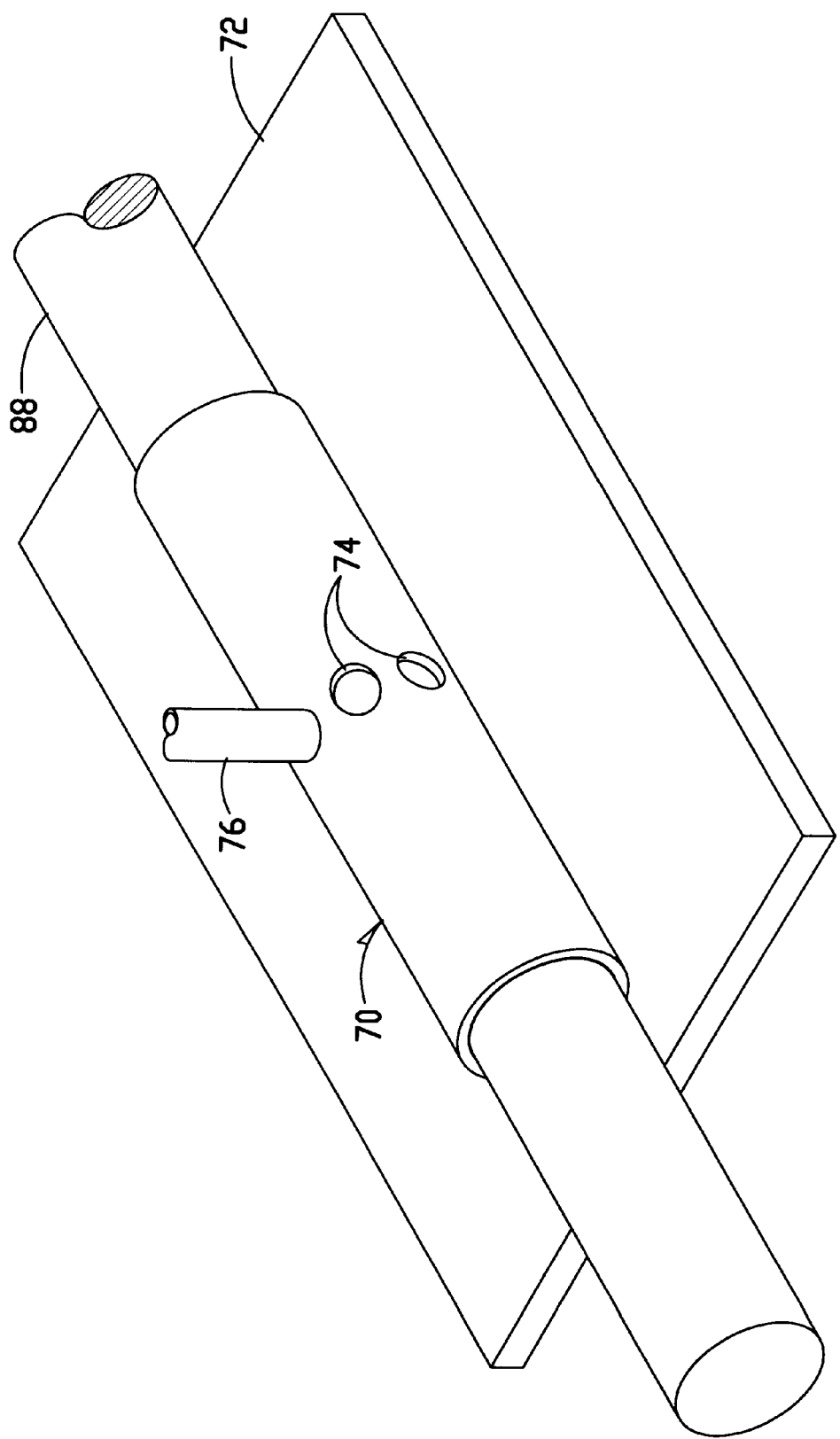
FIG. 11 is a perspective view of a tubular shield being prepared for use in an alternative fashion.

It may also be desirable to provide a shield with an odd number of holes, or with a series of holes that are not symmetrically spaced around the circumference of the tube. For instance, it may be desired to provide conducting areas on only three of the six segments 54 of the electrode tip of FIG. 6. In such cases, a rod 88 may be temporarily inserted in the sleeve 70, as illustrated in FIG. 11. Delron™ rods are suitable for this purpose. The punch 76 will then cut a hole in only one side of the sleeve at a time before being encountering the rod 88.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A method, comprising:

providing an electrode member;

coating a first portion of the electrode member with an electrically insulating material;

providing a tubular shield, where the tubular shield has perforations at selected locations;

placing said shield over at least said first portion of said electrode member;

etching said electrically insulating material exposed through said perforated tubular shield; and removing said shield.

2. The method of claim 1, wherein coating includes coating the first portion with the electrically insulating material that comprises parylene C.

3. The method of claim 1, wherein placing said tubular shield over at least said first portion of said electrode further comprises filling a lumen of said tube with medical adhesive.

4. The method of claim 1, wherein placing said shield comprises expanding said tubular shield.

5. The method of claim 4, wherein expanding said tubular shield comprises treating said shield with heptane.

6. The method of claim 1, wherein providing the tubular shield includes perforating said tubular shield by boring circumferential through bores completely through said tubular shield.

7. The method according to claim 6, wherein perforating said tubular shield comprises placing a rod in a central lumen of said tubular shield, punching holes through said shield to said rod, and removing said rod from said tubular shield.

8. The method of claim 1, wherein removing said shield comprises expanding said tubular shield.

9. The method of claim 8, wherein expanding said tubular shield comprises treating said shield with heptane.

10. The method of claim 1, wherein providing the electrode member includes providing the electrode member coated with iridium oxide.

* * * * *